(12) United States Patent
Janjua

(10) Patent No.: US 10,154,850 B2
(45) Date of Patent: Dec. 18, 2018

(54) NASAL BALLOON CATHETER AND SPONGE UNIT

(71) Applicant: Tanveer Ahmed Janjua, Basking Ridge, NJ (US)

(72) Inventor: Tanveer Ahmed Janjua, Basking Ridge, NJ (US)

( * ) Notice: Subject to any disclaimer, the term of this patent is extended or adjusted under 35 U.S.C. 154(b) by 18 days.

(21) Appl. No.: 15/028,883

(22) PCT Filed: Sep. 23, 2015

(86) PCT No.: PCT/US2015/051706
§ 371 (c)(1),
(2) Date: Apr. 12, 2016

(87) PCT Pub. No.: WO2016/049175
PCT Pub. Date: Mar. 31, 2016

(65) Prior Publication Data
US 2017/0172592 A1    Jun. 22, 2017

Related U.S. Application Data

(60) Provisional application No. 62/055,339, filed on Sep. 25, 2014.

(51) Int. Cl.
*A61F 13/15* (2006.01)
*A61F 13/20* (2006.01)
*A61B 17/24* (2006.01)
*A61M 25/10* (2013.01)
(Continued)

(52) U.S. Cl.
CPC ........ *A61B 17/24* (2013.01); *A61B 17/12045* (2013.01); *A61B 17/12104* (2013.01);
(Continued)

(58) Field of Classification Search
CPC .............. A61B 17/24; A61B 17/12045; A61B 17/12104; A61B 17/12136; A61B 2017/00477; A61B 2017/12004; A61B 17/1204; A61B 17/0057; A61B 2017/00632; A61F 13/2005;
(Continued)

(56) References Cited

U.S. PATENT DOCUMENTS 3,903,893 A * 9/1975 Scheer ............. A61B 17/12045
604/101.05
4,338,941 A 7/1982 Payton
(Continued)

*Primary Examiner* — Andrew J Mensh
(74) *Attorney, Agent, or Firm* — Pepper Hamilton LLP

(57) ABSTRACT

A nasal balloon catheter and sponge unit is provided for stopping posterior epistaxis (nosebleed) in a quick and adjustable manner. The unit can be easily introduced into the bleeding nasal passage of a patient by a health care provider. Once inserted in the patient's nasal passage, the unit operates through inflation of a posterior balloon via a catheter, acting to stop the posterior bleed. In some embodiments, a second (anterior) balloon covers the inside of the nasal passage and is inflated subsequent to the inflation of the posterior balloon. Excess blood coming out of the nasal passage in the front is stopped by an absorbable sponge. If the packing is loose and blood escapes from the back of the nasal passage, a nut is utilized to squeeze the catheter against the nostril, hence more tightly pulling the posterior balloon to stop the blood.

21 Claims, 20 Drawing Sheets

(51) Int. Cl.
*A61B 17/00* (2006.01)
*A61B 17/12* (2006.01)

(52) U.S. Cl.
CPC .... *A61B 17/12136* (2013.01); *A61F 13/2005* (2013.01); *A61B 17/0057* (2013.01); *A61B 17/1204* (2013.01); *A61B 2017/00477* (2013.01); *A61B 2017/00632* (2013.01); *A61B 2017/12004* (2013.01); *A61M 25/1011* (2013.01); *A61M 2025/1052* (2013.01); *A61M 2210/0618* (2013.01); *A61M 2210/0681* (2013.01)

(58) Field of Classification Search
CPC .. A61M 2025/1052; A61M 2210/0618; A61M 2210/0681; A61M 25/1011
USPC .................................................. 604/385.01
See application file for complete search history.

(56) References Cited

U.S. PATENT DOCUMENTS

| | | | |
|---|---|---|---|
| 5,139,510 A | 8/1992 | Goldsmith, III et al. | |
| 5,207,651 A * | 5/1993 | Snyder | A61M 25/02 604/174 |
| 7,108,706 B2 | 9/2006 | Hogle | |
| 7,909,845 B2 | 3/2011 | Ashenhurst | |
| 2002/0058960 A1* | 5/2002 | Hudson | A61B 17/0057 606/192 |
| 2004/0230156 A1* | 11/2004 | Schreck | A61L 27/50 604/96.01 |
| 2004/0243172 A1* | 12/2004 | Hogle | A61B 17/24 606/199 |
| 2008/0142003 A1* | 6/2008 | Depel | A61M 16/0429 128/200.24 |

\* cited by examiner

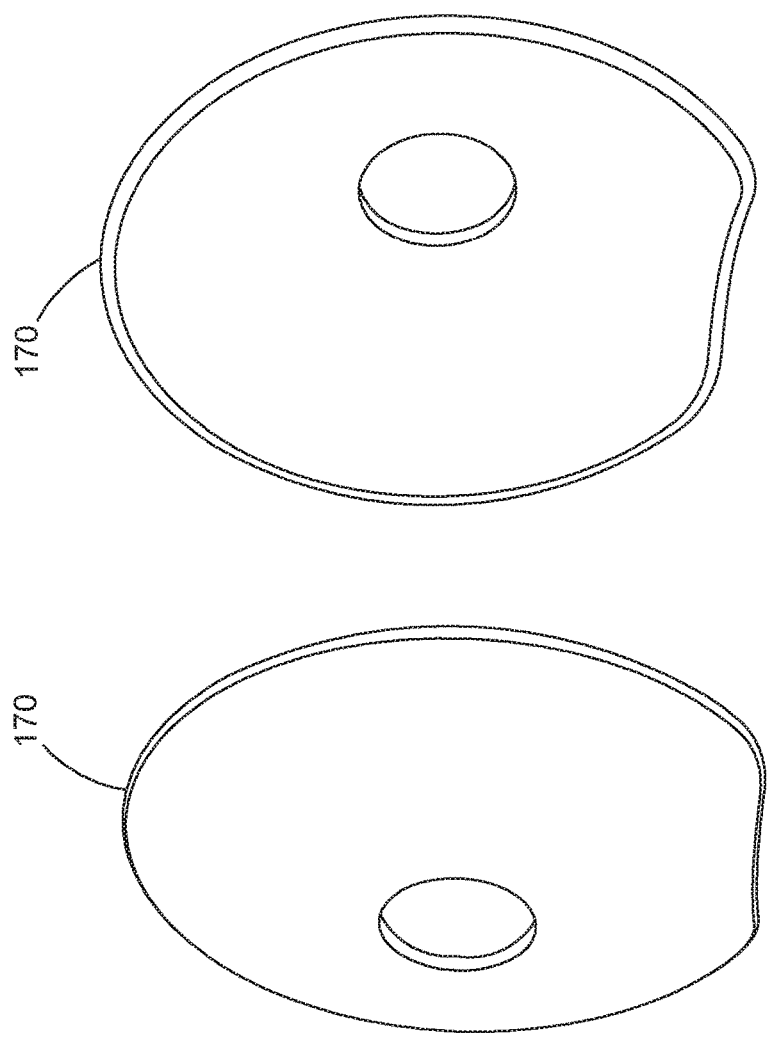

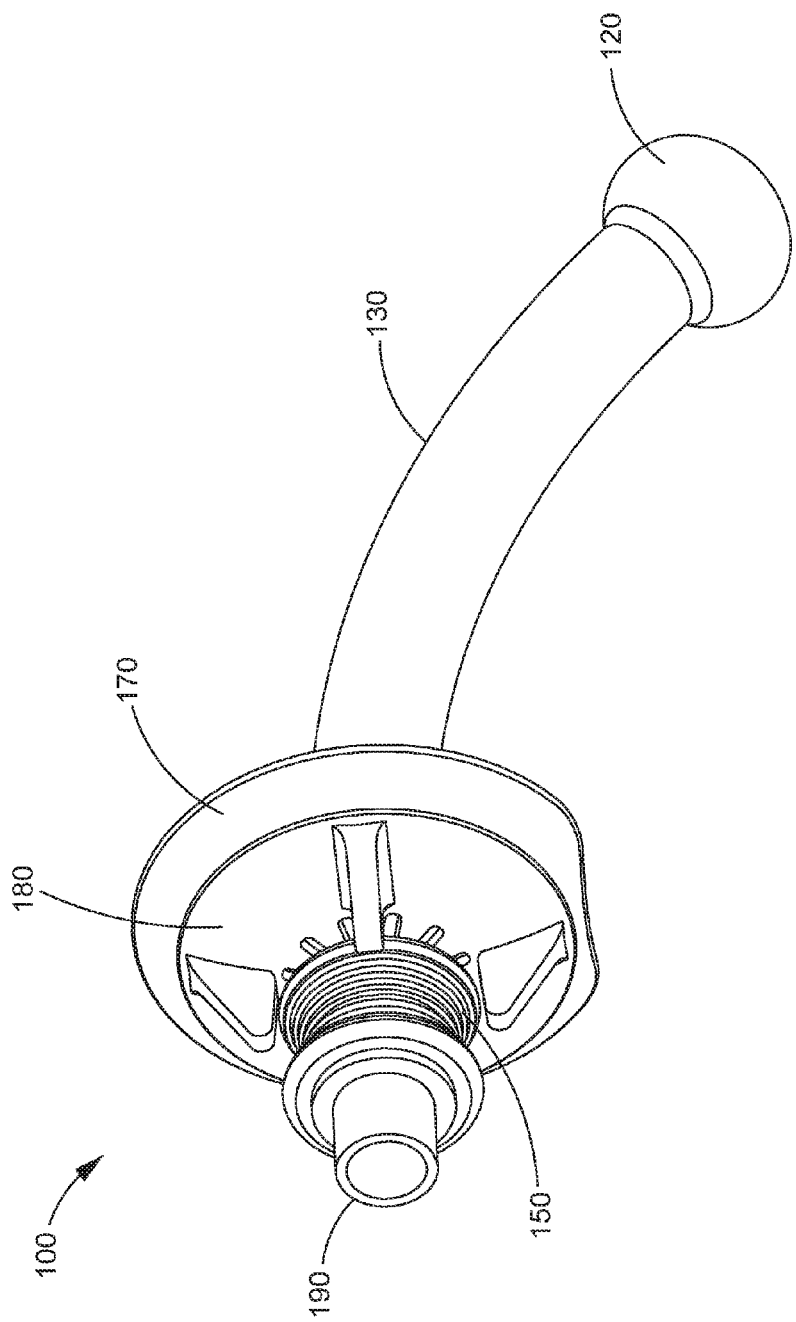

NASAL BALLOON CATHETER AND SPONGE UNIT

CROSS-REFERENCE TO RELATED APPLICATIONS

This application is a U.S. National Phase filing of International Application No. PCT/US2015/051706, filed on Sep. 23, 2015, which claims priority to U.S. Provisional Patent Application No. 62/055,339, filed Sep. 25, 2014, both entitled "Nasal Balloon Catheter and Sponge Unit," the contents of which are herein incorporated by reference in their entirety.

TECHNOLOGY FIELD

This disclosure relates generally to a device to stop posterior epistaxis, and more particularly to a nasal balloon catheter and sponge unit for stopping posterior epistaxis.

BACKGROUND

Epistaxis (nosebleed) is a very common problem in the general public. Epistaxis can be divided into two types: anterior (front) epistaxis and posterior (back) epistaxis. Anterior epistaxis is the more common type. It originates in front part of the nasal cavity and can be easily controlled by pressure applied to the external nose by proper prolonged pinching or pressure applied from inside by the use of a nasal packing. This is possible because the blood vessels in the front of the nose that usually cause this bleeding are small in size and easily compressible. Posterior epistaxis is more severe for two reasons: 1) it is generally caused by a larger blood vessel; and 2) it is located posteriorly in an area that is difficult to compress.

Typically, patients who suffer from a posterior epistaxis are elderly individuals who suffer from hypertension and sometimes are also on blood thinning medication that makes it even more difficult for the blood to naturally clot and the bleeding to stop. In these individuals, excessive blood loss can lead to heart attack, stroke, pneumonia, and even death. The goal is to stop the bleeding as soon as possible. This can typically be easily accomplished by an experienced Otolaryngologist (Ear, Nose and Throat Specialist). However, in many situations the only healthcare provider available is an EMT (Emergency Medical Technician), paramedic, nurse, or an emergency room physician. The devices available at present are not user friendly and/or efficient.

Therefore, a device that can maintain pressure on a catheter body system, is small in diameter allowing for easy insertion, has one port only, and is adjustable in terms of the pressure that can be applied, is desired.

SUMMARY

Embodiments provide for a nasal balloon catheter and sponge unit that stops posterior epistaxis (nosebleed).

In an embodiment, a nasal balloon catheter and sponge unit comprises: a catheter core body comprising an anterior portion and a posterior portion; a luer lock connected to the catheter core body via a threaded portion attached to an anterior-most portion of the catheter core body; an inflation port connected to an anterior end of the luer lock; a posterior balloon surrounding at least a portion of the posterior portion of the catheter core body; an anterior balloon surrounding at least a portion of the anterior portion of the catheter core body; an expandable sponge positioned around the anterior-most portion of the catheter core body; a washer positioned and moveable adjacent and anterior to the sponge on the threaded portion; and an adjustable nut positioned and moveable adjacent and anterior to the washer on the threaded portion. The catheter core body is insertable into a nasal passage of a patient; and a passageway extends from the inflation port, through the luer lock, through the threaded portion, and through the catheter core body, allowing for a fluid to be introduced through the inflation port and travel through the passageway, exiting at an exit hole located in the posterior portion of the catheter core body to inflate first the posterior balloon and then the anterior balloon.

In an embodiment, the posterior balloon is of a thinner thickness than the anterior balloon, providing for the posterior balloon to inflate prior to the anterior balloon.

In an embodiment, the expandable sponge comprises a central hole and a hemi-domed shape with its base facing anteriorly; wherein the expandable sponge is configured to conform to an inside portion of a nostril of the patient when the catheter core body is inserted into the nasal passage of the patient.

In an embodiment, the washer comprises a central hole, a soft material, is sized larger than a nostril of the patient, and is of a substantially round shape with a curved portion at a bottom portion that comes into contact with the patient.

In an embodiment, the adjustable nut is configured to be pushed over the threaded portion to compress the sponge and apply pressure thereto. In another embodiment, the adjustable nut is further configured to decrease pressure on the sponge. In an embodiment, the adjustable nut is one of a rotating nut or a speed nut.

According to an additional embodiment, a nasal balloon catheter and sponge unit comprises: a catheter core body comprising an anterior portion and a posterior portion; a luer lock connected to the catheter core body via a threaded portion attached to an anterior-most portion of the catheter core body; an inflation port connected at an anterior end of the luer lock; a posterior balloon surrounding at least a portion of the posterior portion of the catheter core body; an expandable sponge surrounding at least a portion of the anterior portion of the catheter core body; a washer positioned and moveable adjacent and anterior to the expandable sponge on the threaded portion; and an adjustable nut positioned and moveable adjacent and anterior to the washer on the threaded portion. The catheter core body is insertable into a nasal passage of a patient; and a passageway extends from the inflation port, through the luer lock, through the threaded portion, and through the catheter core body, allowing for a fluid to be introduced through the inflation port and travel through the passageway, exiting at an exit hole located in the posterior portion of the catheter core body to inflate the posterior balloon.

In an embodiment, the expandable sponge comprises a central hole and is oval shaped, tapering at its ends and expanding anteriorly into a hemi-dome shape at the anterior-most portion of the catheter core body to conform to the inside of a nostril of the patient when the catheter core body is inserted into the nasal passage of the patient.

In an embodiment, the oval shaped portion and the hemi-domed shaped portion of the expandable sponge comprise a single unit.

In an embodiment, the expandable sponge surrounds a majority portion of the anterior portion of the catheter core body.

Additional features and advantages of this disclosure will be made apparent from the following detailed description of illustrative embodiment that proceeds with reference to the accompanying drawings.

BRIEF DESCRIPTION OF THE DRAWINGS

The foregoing and other aspects of the invention are best understood from the following detailed description when read in connection with the accompanying drawings. The drawings depict embodiments solely for the purpose of illustration, it should be understood, however, that the disclosure is not limited to the specific instrumentalities disclosed. Included in the drawings are the following Figures:

FIGS. 1A-1E are an exploded view and individual component views of a nasal balloon catheter and sponge unit, according to an embodiment;

FIGS. 4A-4F illustrate views of a nasal balloon catheter and sponge unit in an inflated state, according to an embodiment;

DETAILED DESCRIPTION

Embodiments provided herein are directed to a nasal balloon catheter and sponge unit for stopping posterior epistaxis (nosebleed). The nasal balloon catheter and sponge unit provides a quick and adjustable mechanism for stopping a posterior bleed. The unit can be easily introduced into the bleeding nasal passage of a patient by a health care provider. Once inserted in the patient's nasal passage, the unit operates through inflation of a posterior balloon via a catheter, acting to stop the posterior bleed. In some embodiments, a second (anterior) balloon covers the inside of the nasal passage and is inflated subsequent to the inflation of the posterior balloon. Excess blood coming out of the nasal passage in the front is stopped by an absorbable sponge. If the packing is loose and blood escapes from the back of the nasal passage, a lug is utilized to squeeze the catheter against the nostril, hence more tightly pulling the posterior balloon to stop the blood. The nasal balloon catheter and sponge unit according to embodiments provided herein addresses two critical issues facing a nosebleed patient and his or her health care provider: 1) immediate control of the bleeding to avoid excess blood loss; and 2) adjustment of the packing without having to remove the unit. Embodiments are described in greater detail in the following description with reference to the figures as indicated.

Figure 1A:
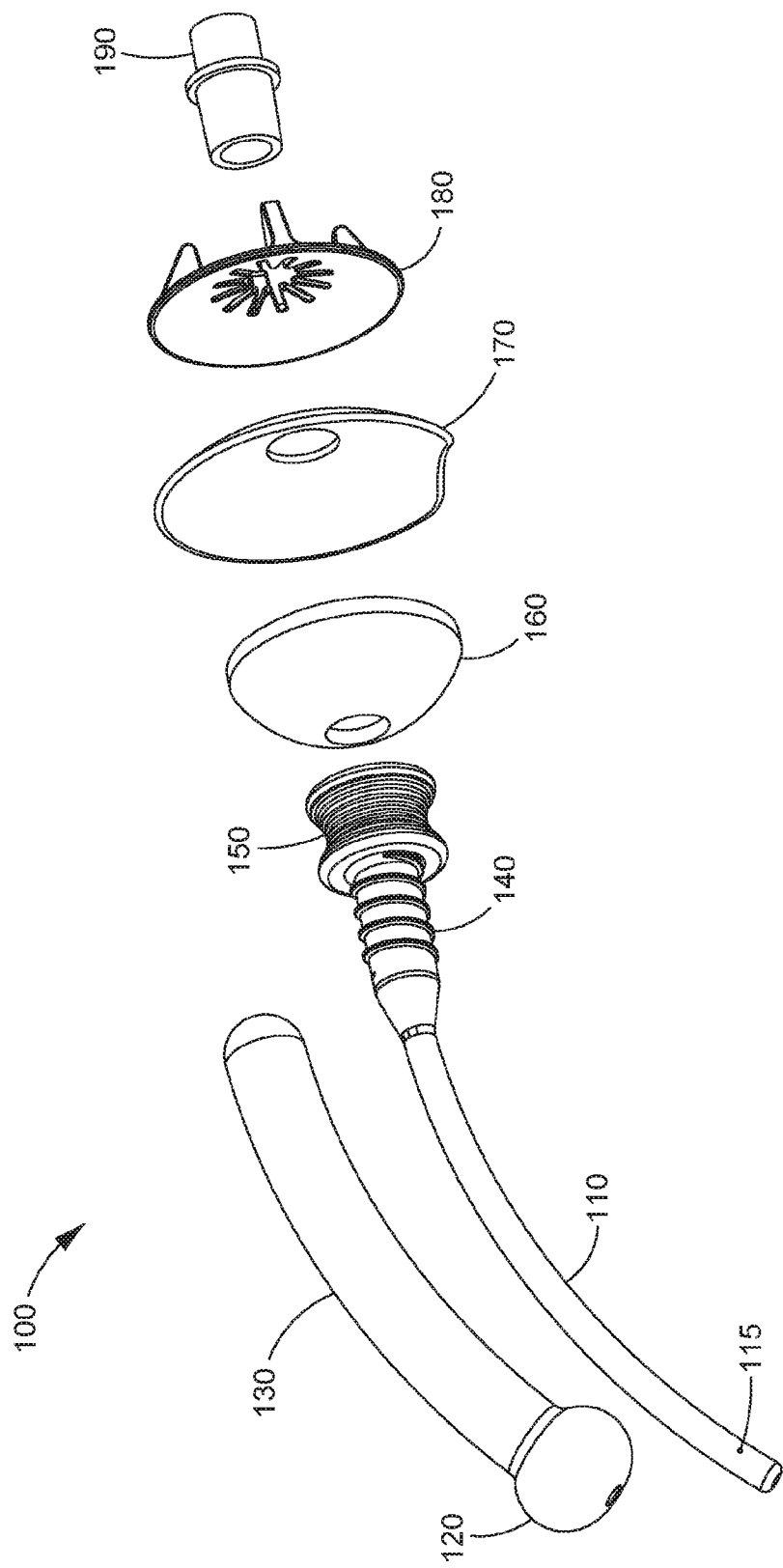
Figure 1B:
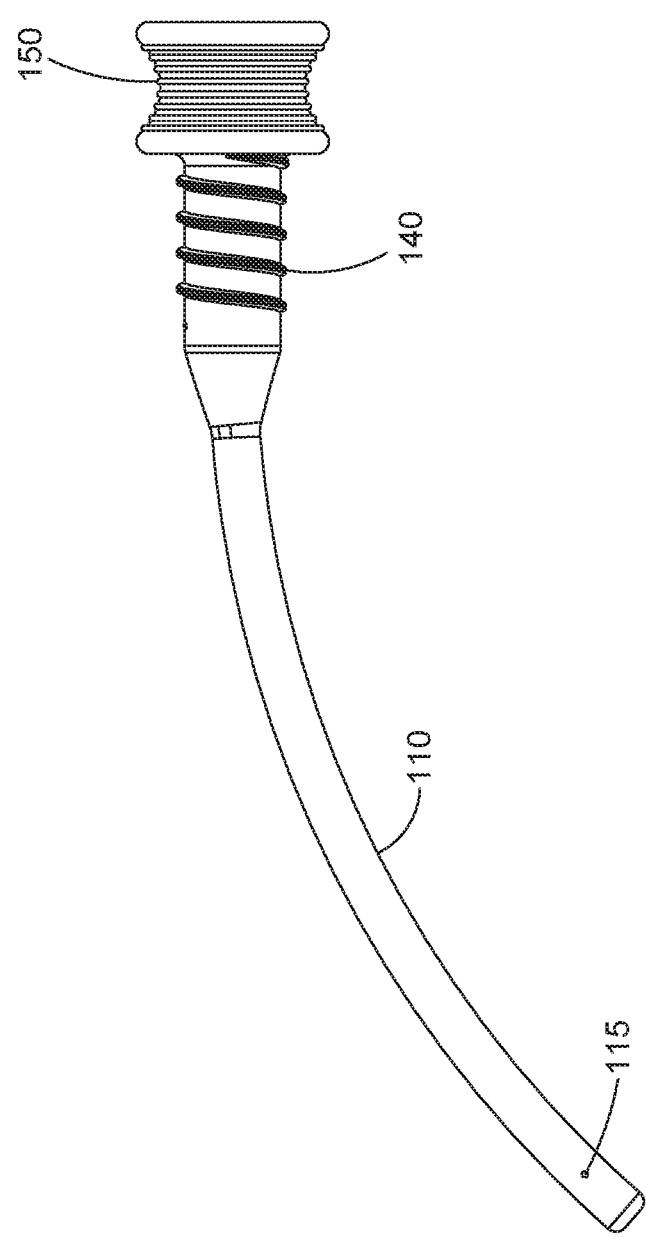
Figure 1C:
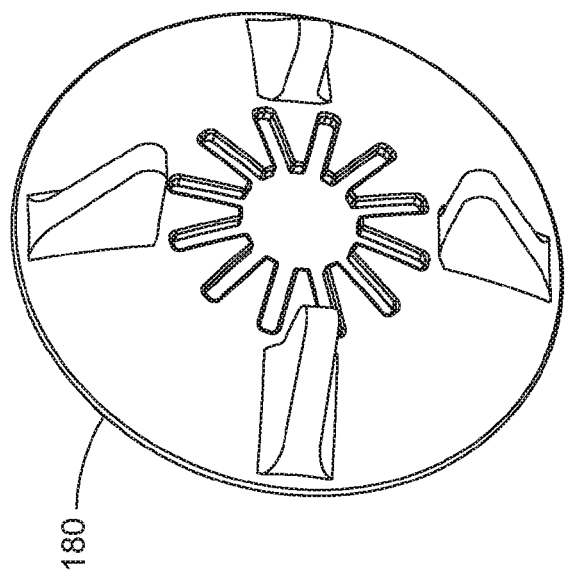
Figure 1C:
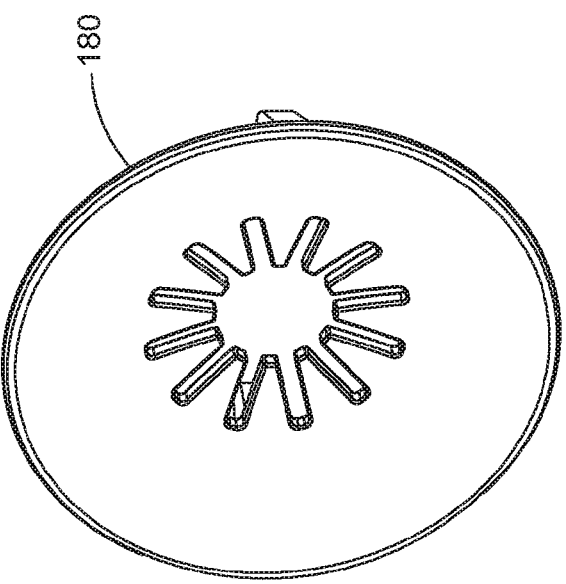
Figure 1D:
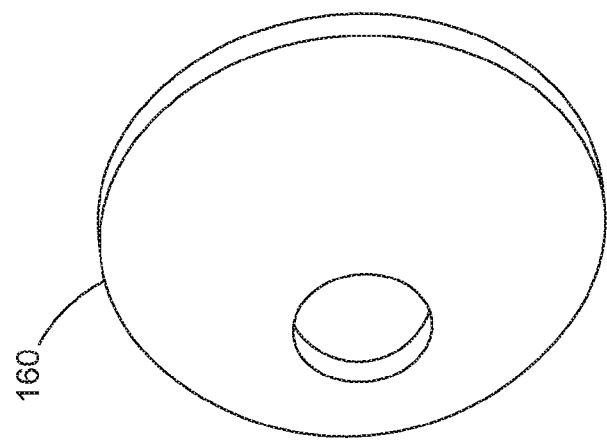
Figure 1D:
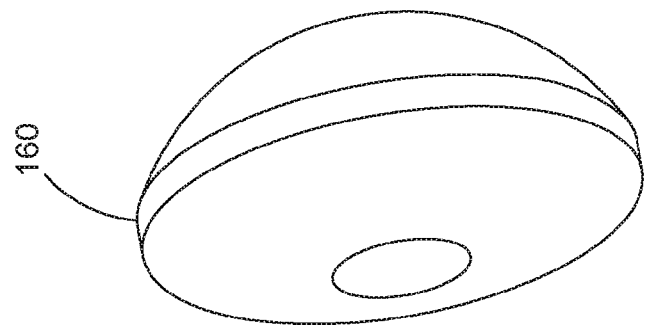
Figure 2A:
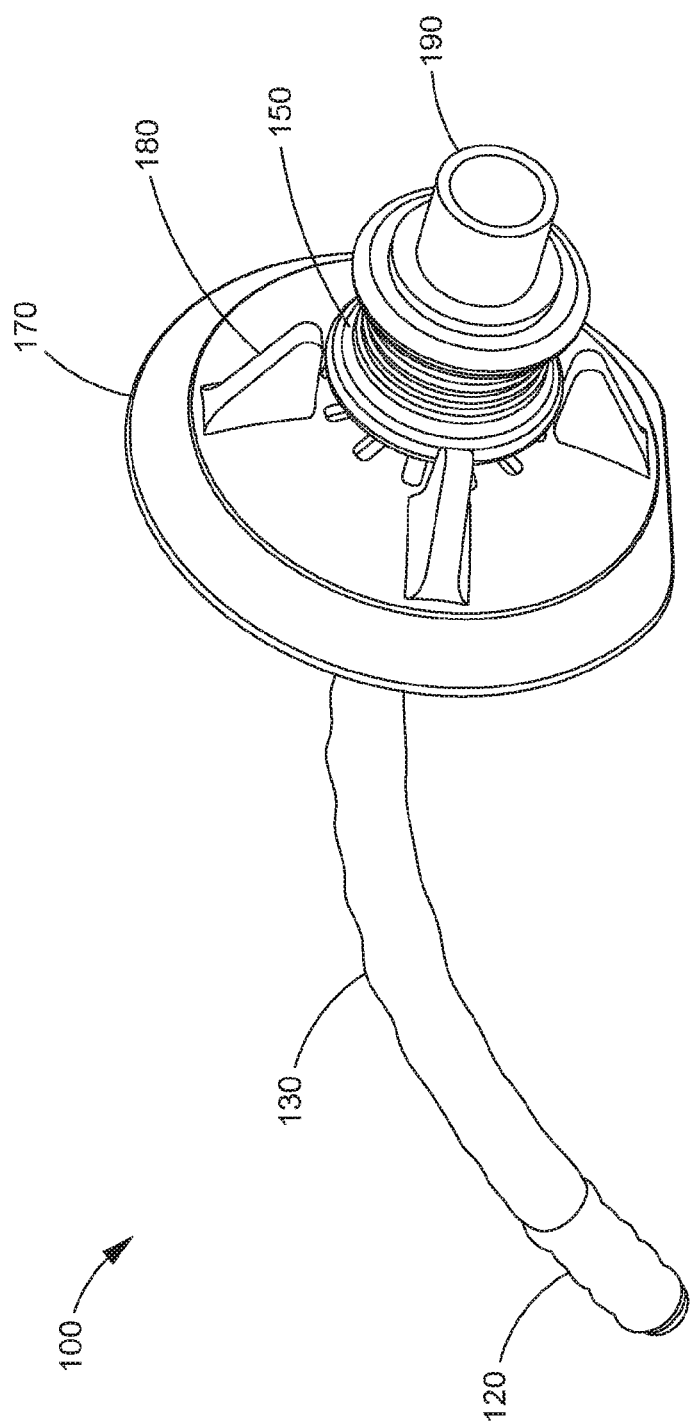
FIGS. 2A-2B illustrate views of a nasal balloon catheter and sponge unit in an uninflated state, according to an embodiment.
Figure 2B:
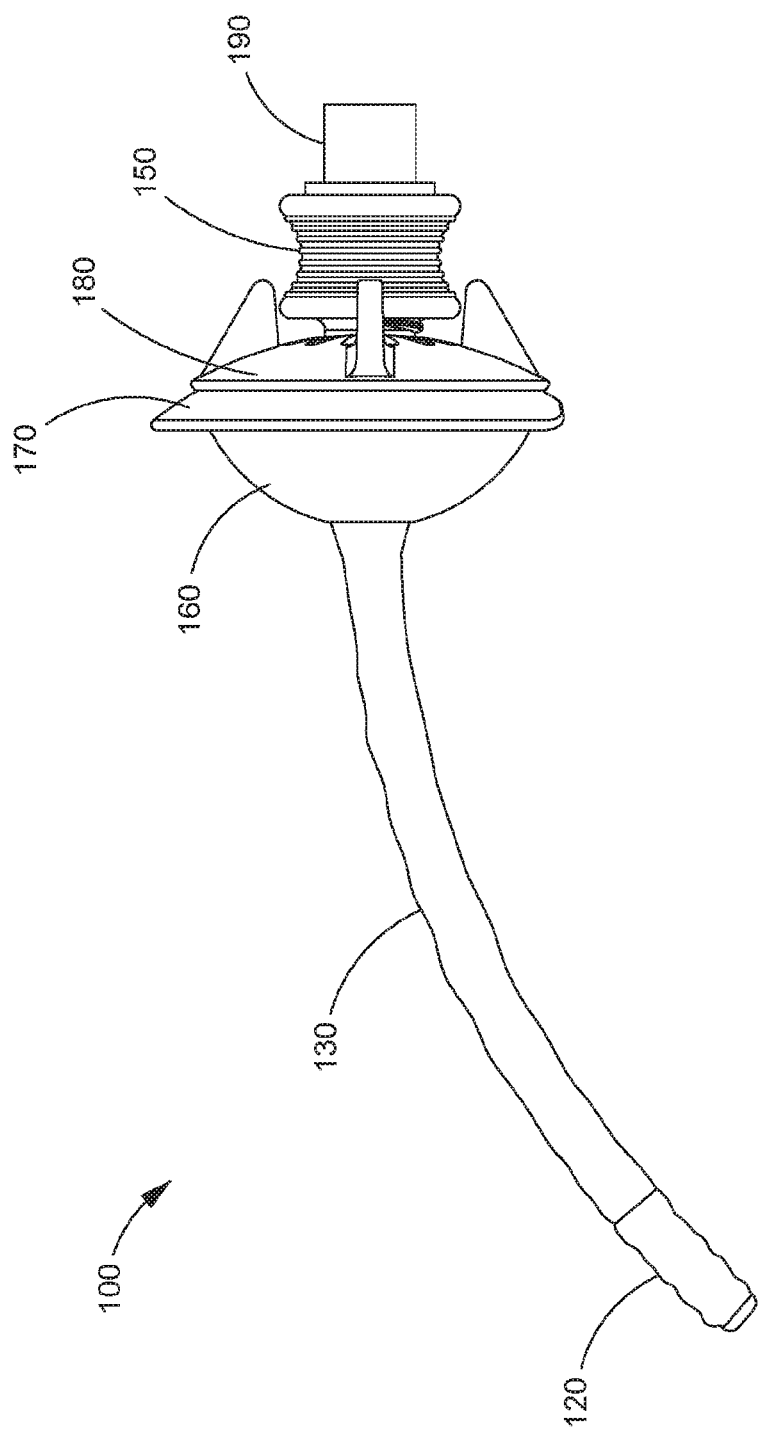
Figure 3A:
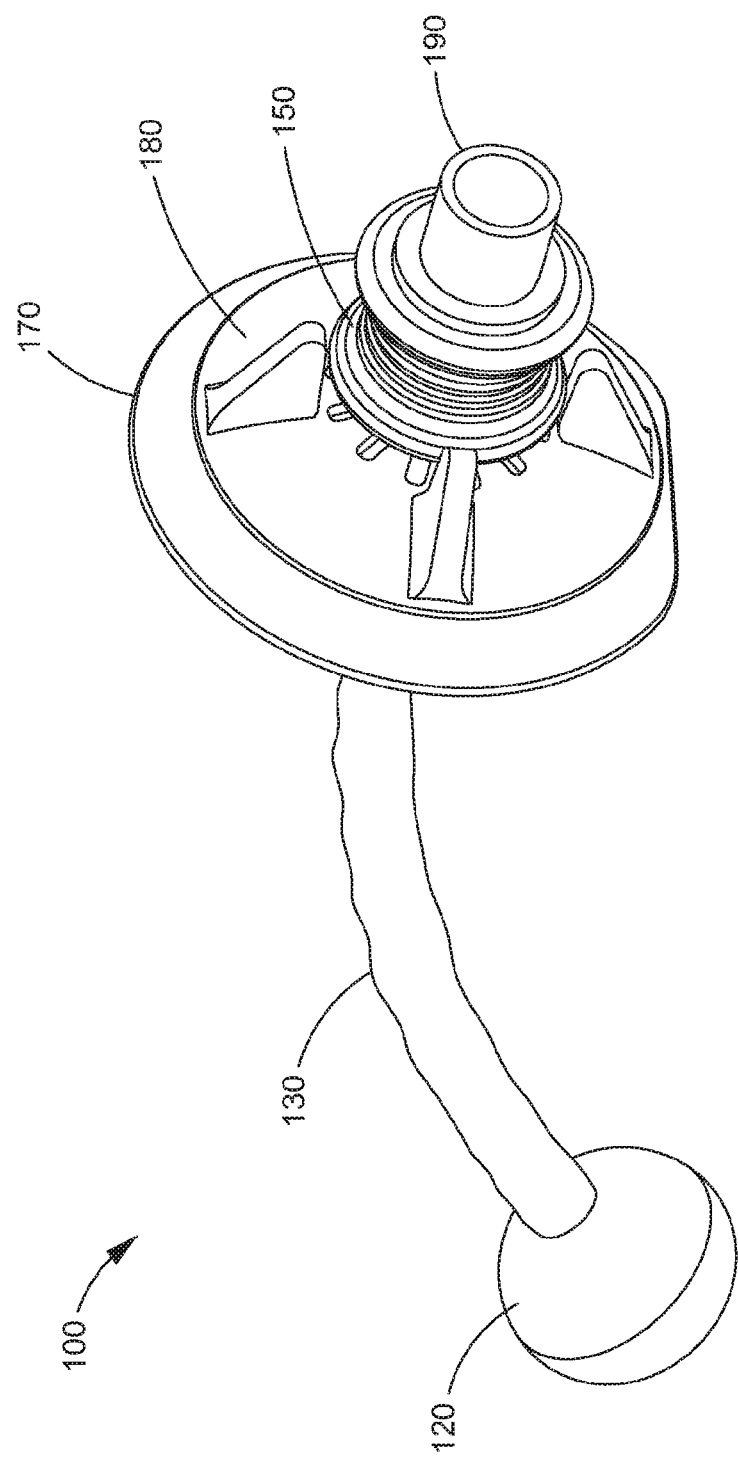
FIGS. 3A-3B illustrate views of a nasal balloon catheter and sponge unit in a partially inflated state, according to an embodiment.
Figure 3B:
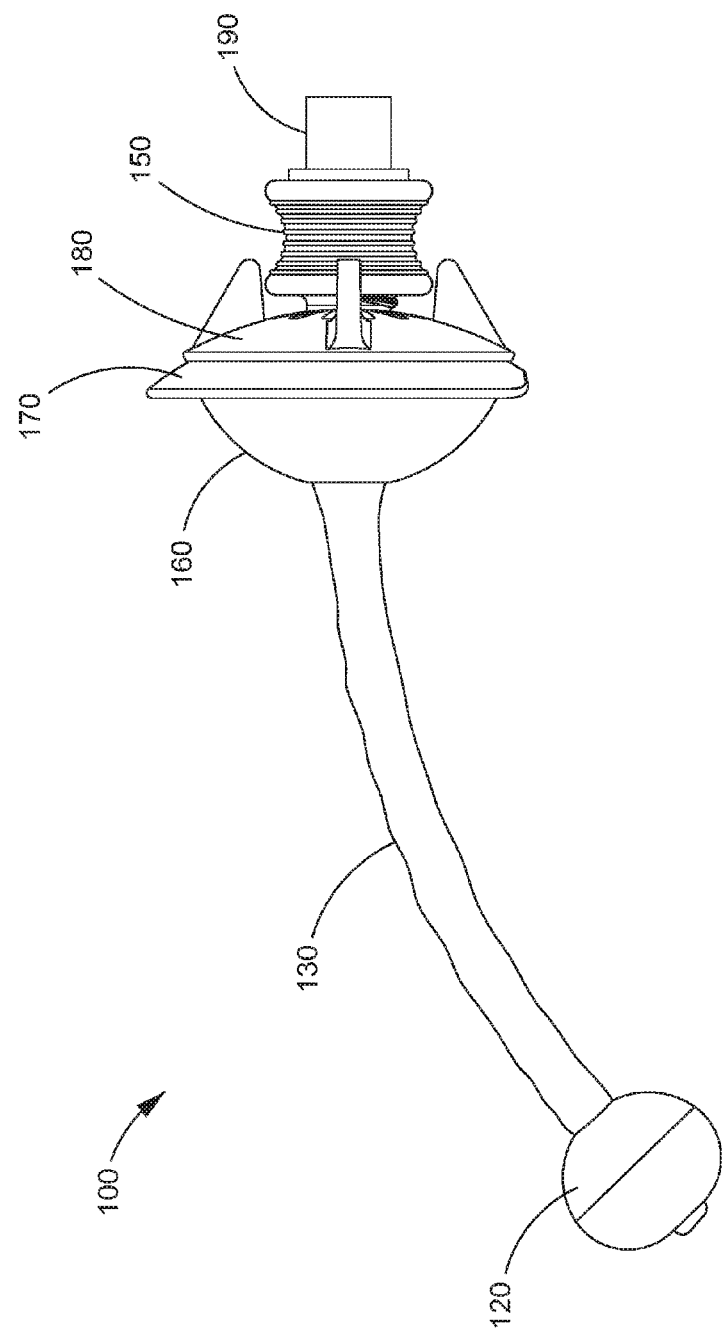

With reference to FIGS. 1A-1E, an exploded view (FIG. 1A) and individual component views (FIGS. 1B-1E) of a nasal balloon catheter and sponge unit 100, according to an embodiment, are provided. Assembled views of the nasal balloon catheter and sponge unit 100 are shown in FIGS. 2A-2B (uninflated state), FIGS. 3A-3B (partially inflated state), FIGS. 4A-4F (fully inflated state), and FIGS. 5A-5B (cross-sectional view).

A catheter core body 110 has an anterior (front) portion and a posterior (back) portion. The catheter core body 110 is formed of a flexible but firm material (e.g., plastics), allowing for some deformation to increase ease of use (e.g., for insertion and placement in the nasal passage).

According to an embodiment, a posterior balloon 120 surrounds at least a portion of the posterior portion of the catheter core body 110, and an anterior balloon 130 surrounds at least a portion of the anterior portion of the catheter core body 110.

As shown, a luer lock 150 is connected to the catheter core body 110 via a threaded portion 140 attached to the anterior-most portion of the catheter core body 110. A single, central inflation port 190 is connected or otherwise attached at an anterior end of the luer lock 150.

As shown, an expandable sponge 160 is positioned and/or positionable around the anterior-most part of the catheter core body 110; a washer 170 is positioned and/or positionable adjacent and anterior to the sponge 160 on the threaded portion 140; and an adjustable nut 180 is positioned and/or positionable adjacent and anterior to the washer 170 on the threaded portion 140.

A passageway extends from the inflation port 190, through the luer lock 150, through the threaded portion 140, and through the catheter core body 110 (see FIG. 5B), allowing for a flow to be introduced through the inflation port 190 and travel through the passageway, exiting at an exit hole 115 located in the posterior portion of the catheter core body 110 to inflate first the posterior balloon 120 and then the anterior balloon 130. A fluid, including liquids (e.g., water or saline) and/or gases (e.g., air), may be used as the flow to inflate the balloons 120, 130. The fluid is, according to an embodiment, provided via a syringe inserted into the inflation port 190. The inflation port 190 may have curved impressions for a thumb and a finger to be fitted into, allowing for the health care provider to have a secure grip on the unit 100. Additionally, the curved impressions may comprise raised, cross-hatched serrations, or the like, to provide friction and avoid slipping of the thumb and the finger. The single port (i.e., the inflation port 190) makes the inflation quicker than devices with multiple ports, thereby simplifying the process to stop posterior nosebleed. In alternate embodiments, a multi-port unit may be used.

According to an embodiment, the posterior balloon 120 and the anterior balloon 130 are a continuous structure, but the posterior balloon 120 is of a thinner thickness than the anterior balloon 130, providing for the posterior balloon 120 to inflate prior to the anterior balloon 130 via the exit hole 115. In an alternative embodiment, a diverter valve is incorporated in the catheter core body 110 to inflate first the posterior balloon 120 and then the anterior balloon 130.

Figure 4A:
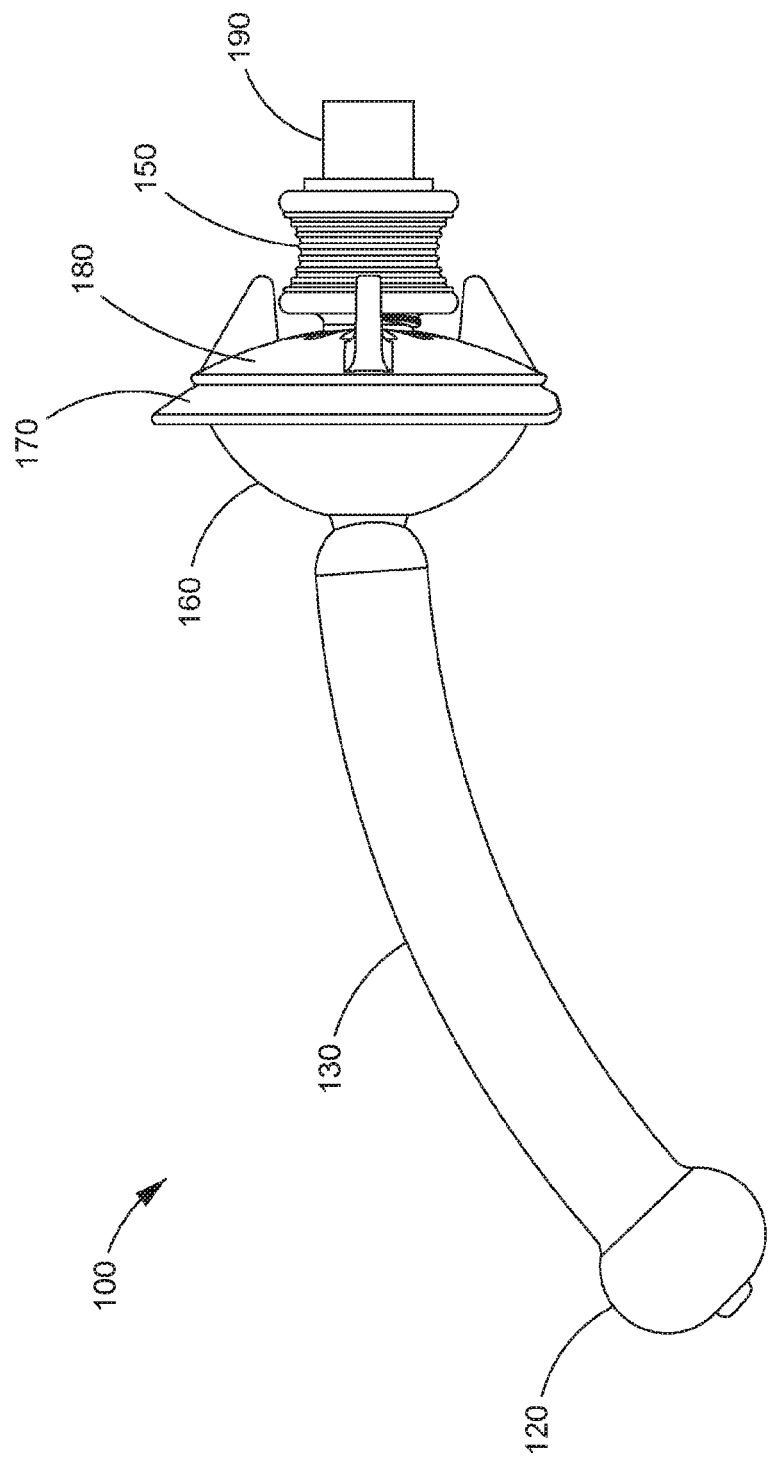
Figure 4B:
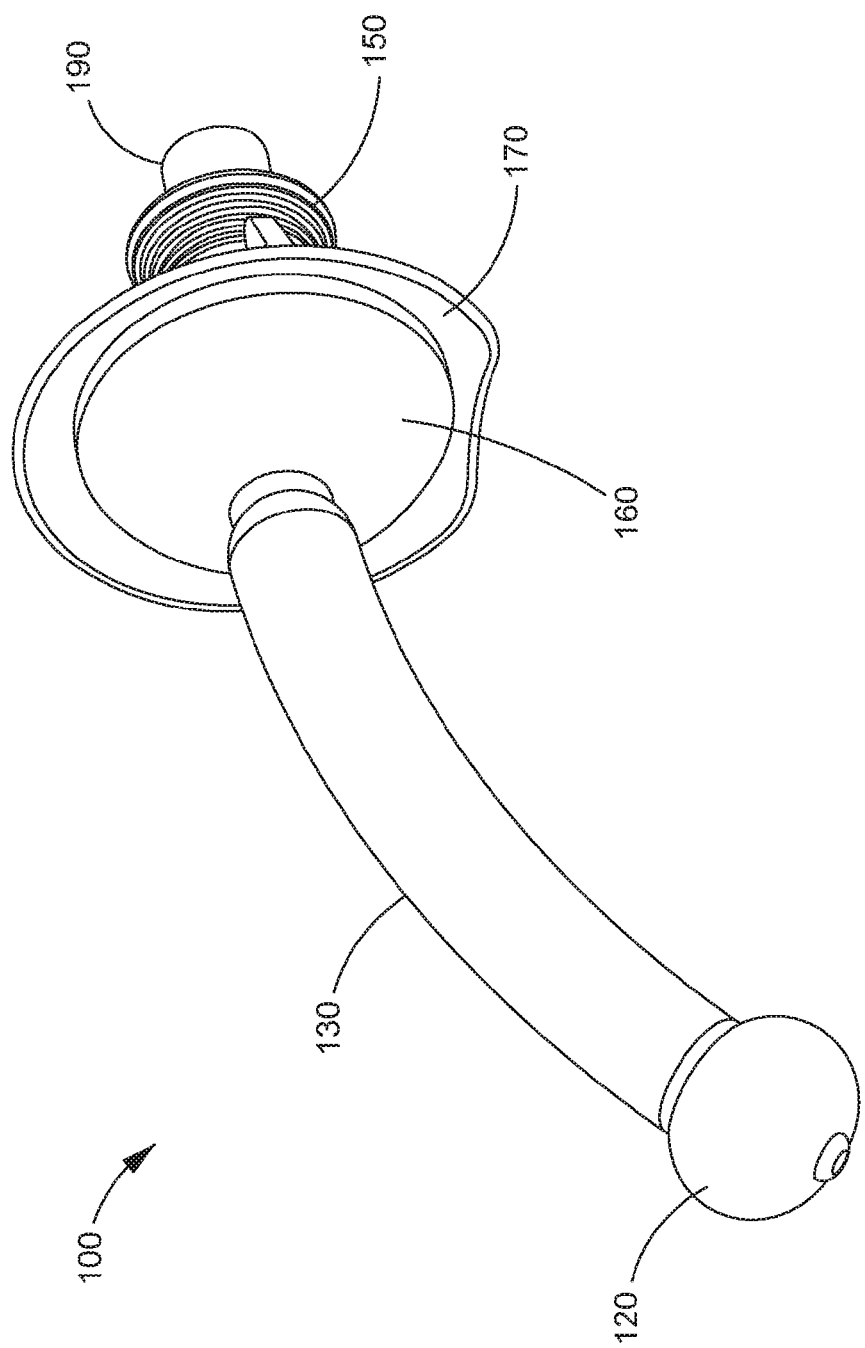
Figure 4D:
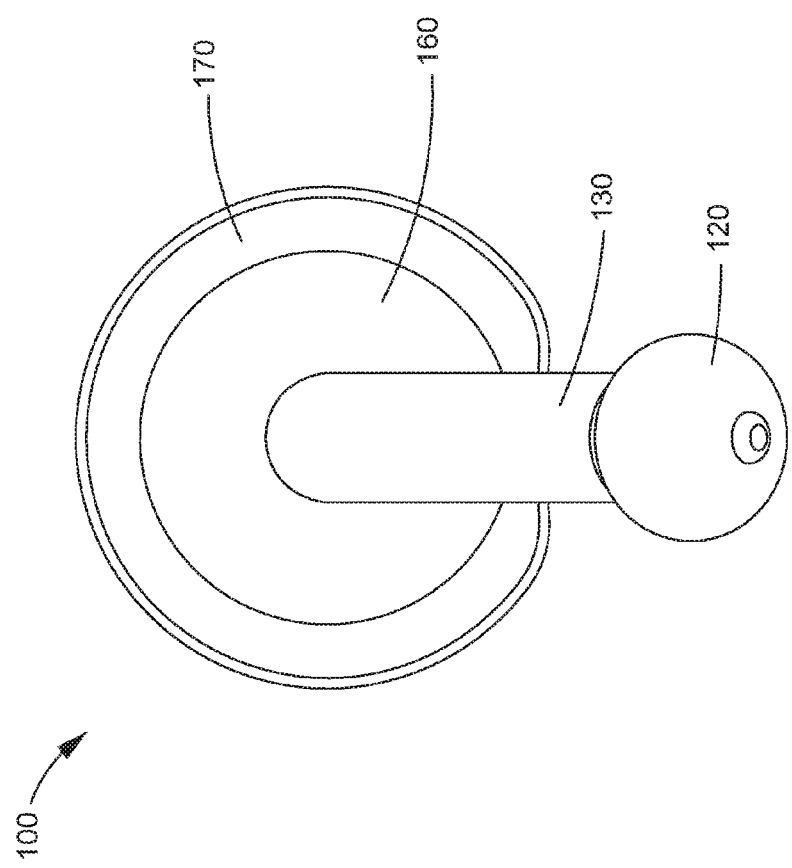
Figure 4E:
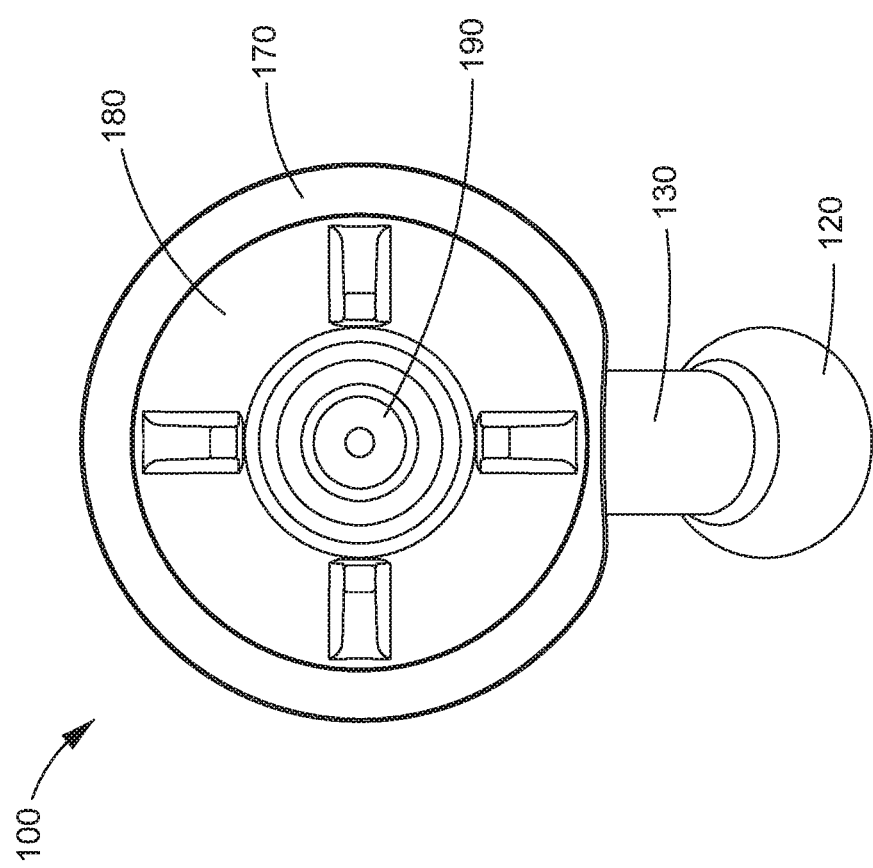
Figure 4F:
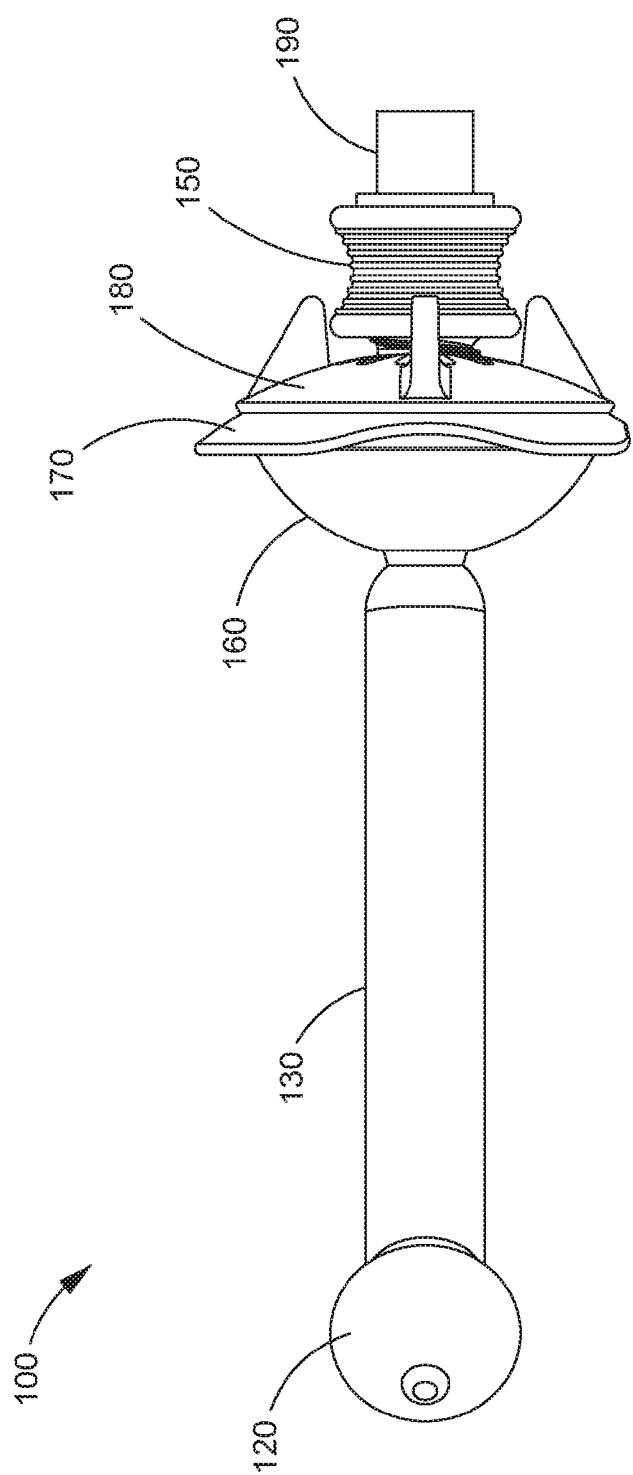
Figure 5A:
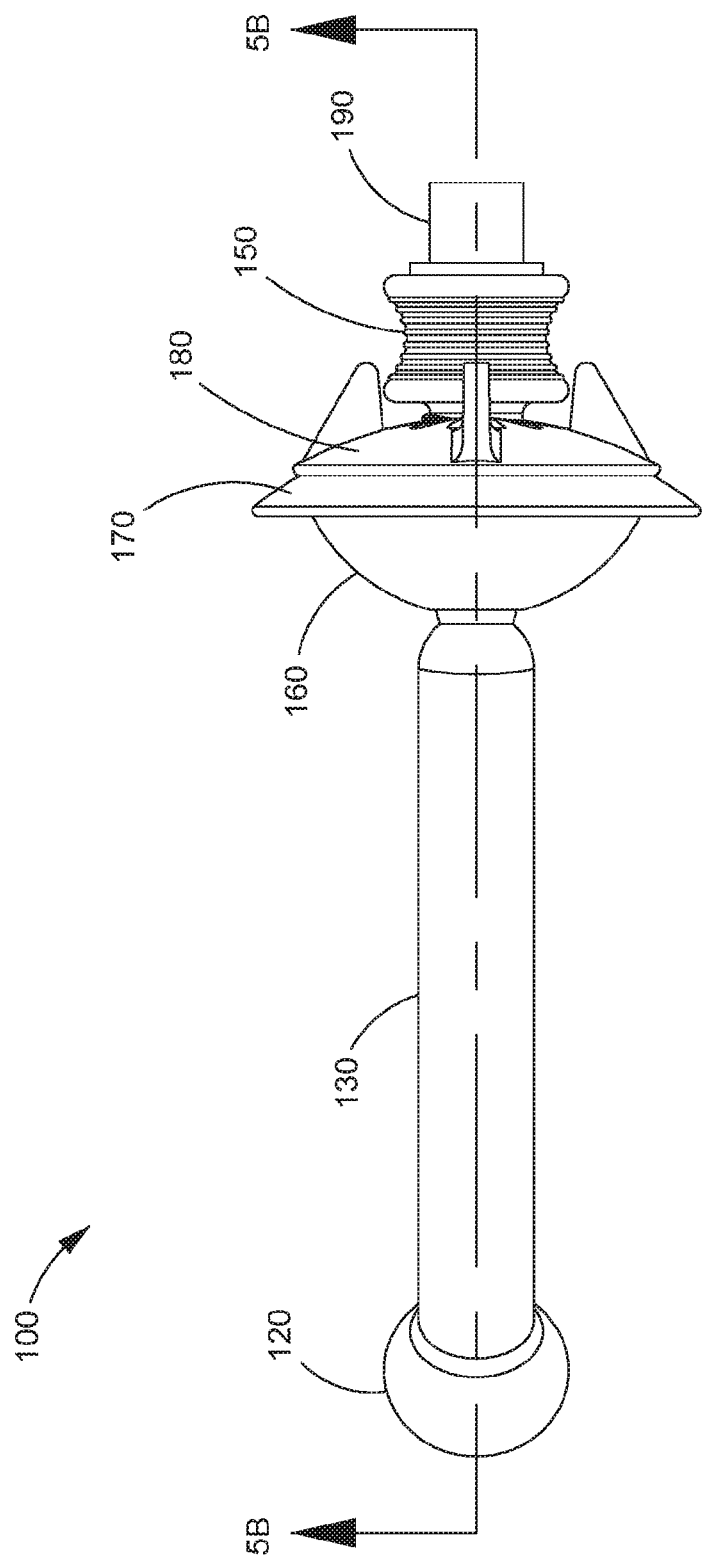
FIGS. 5A-5B provide a cross-sectional view of a nasal balloon catheter and sponge unit in an inflated state, according to an embodiment.
Figure 5B:
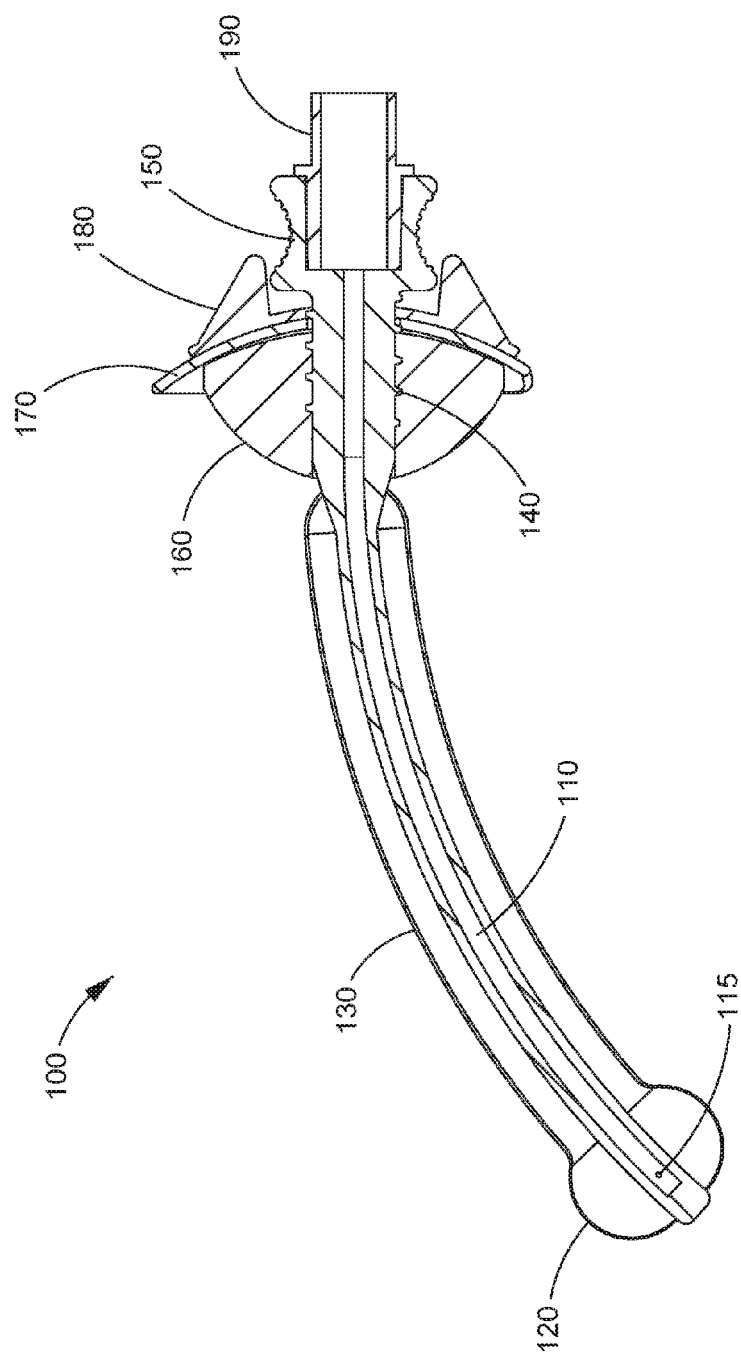

In an embodiment, as shown, the posterior balloon 120 is of a substantially spherical shape, while the anterior balloon 130 is of a substantially three-dimensional oval shape, until its anterior end portion where it tapers down near the expandable sponge 160, as shown (see, e.g., FIG. 4A). In other embodiments, the anterior balloon 130 is of a substantially three-dimensional elliptical or rectangular shape, again tapering down at its anterior end portion. Additionally, in an embodiment, the posterior balloon 120 is of an overall smaller size (volume-wise) than the anterior balloon 130. As the posterior balloon 120 is being inflated, it is being wedged behind the posterior nasal choana to stop the posterior bleed. As the anterior balloon 130 is being inflated, after pressure becomes high in the posterior balloon 120, the anterior balloon 130 covers the inside of the nasal passage of the patient.

The expandable sponge 160, positioned around the anterior-most part of the catheter core body 110, has a central hole that allows for the catheter core body 110 to move back and forth with respect to the expandable sponge 160, hence allowing compression of the sponge 160. In an embodiment, the expandable sponge 160 is in the shape of a hemi-dome with its base facing anteriorly, as shown. The hemi-dome shape fits well into a nostril of the patient, allowing the expandable sponge 160 to conform to the inside of the nostril when the catheter core body 110 is inserted into the nasal passage of the patient. The flat base of the expandable sponge 160 is positioned against and in contact with the washer 170, allowing for compression with posterior movement of the washer 170.

The washer 170 has a central hole that allows for the catheter core body 110 to move back and forth with respect to the washer 170, and is positioned anterior to the expandable sponge 160 on the threaded portion 140. The washer 170 is formed from a soft, flexible material, such as silicon or rubber. The washer 170, according to an embodiment, is of a substantially round shape with a curved flat base to allow it to rest on the upper lip of the patient without digging into the patient's skin. The washer 170 is sized larger than the nostril of the patient, thereby wedging against the nostril and squeezing the sponge 160 when being posteriorly pushed by the adjustable nut 180 over the threaded portion 140. The posterior pushing movement generates a stronger seal of the posterior nasal choana by the posterior balloon 120, thus helping with stopping the nose bleed.

The adjustable nut 180, positioned adjacent and anterior to the washer 170 on the threaded portion 140 and behind the luer lock 150, is configured to compress the expandable sponge 160 and apply pressure thereto, and also be adjusted to decrease pressure therefrom. In one embodiment, the adjustable nut 180, when positioned on the threaded portion 140, is able to be twisted posteriorly to apply pressure. Alternatively, the adjustable nut 180 can be pushed posteriorly with manual pressure (while the heath care provider holds onto the inflation port 190 for support).

In one embodiment, the adjustable nut 180 is a speed nut that can be pushed over the threaded portion 140 and locked in one-way. The speed nut can be tightened by posteriorly pushing, and can be relaxed by rotation to match with protrusions of the threaded portion 140 to move anteriorly and hence decrease pressure.

In another embodiment, the adjustable nut 180 is a rotating nut (i.e., a hexagonal nut), that can be moved posteriorly over the threaded portion 140.

The nasal balloon catheter and sponge unit 100, according to embodiments provided herein, functions as follows: the inflation port 190 is grasped and the catheter core body 110 (with the posterior balloon 120 and anterior balloon 130) is inserted in a nasal passage of a patient. Fluid is introduced via a syringe into the inflation port 190 and travels through the passageway. Via the exit hole 115, the posterior balloon 120 is inflated (see FIGS. 3A-3B), and once enough pressure is generated in the posterior balloon 120, the anterior balloon 130 is inflated (see FIGS. 4A-4F). According to an embodiment, the anterior balloon 130 covers roughly two-thirds of a patient's anterior nasal cavity. The expandable sponge 160, when fully swollen, conforms to the inside of the patient's nostril. The washer 170 wedges against the nose, avoiding any posterior pull on the unit 100 that could loosen the posterior seal and allow the blood to drip in the throat. The adjustable nut 180 can be quickly pushed over the one way tilted thread (the threaded portion 140) to compress the sponge 160 and increase the pressure on the catheter core body 110 while protecting the nostril rim with the washer 170. The speed nut is designed in such a way that rotating it in the counterclockwise direction will align the gaps on the nut with the crevices of the thread to allow pulling it back to decrease the pressure. In an alternate embodiment, a rotating nut over the threaded portion 140 can push against the washer 170.

Figure 6A:
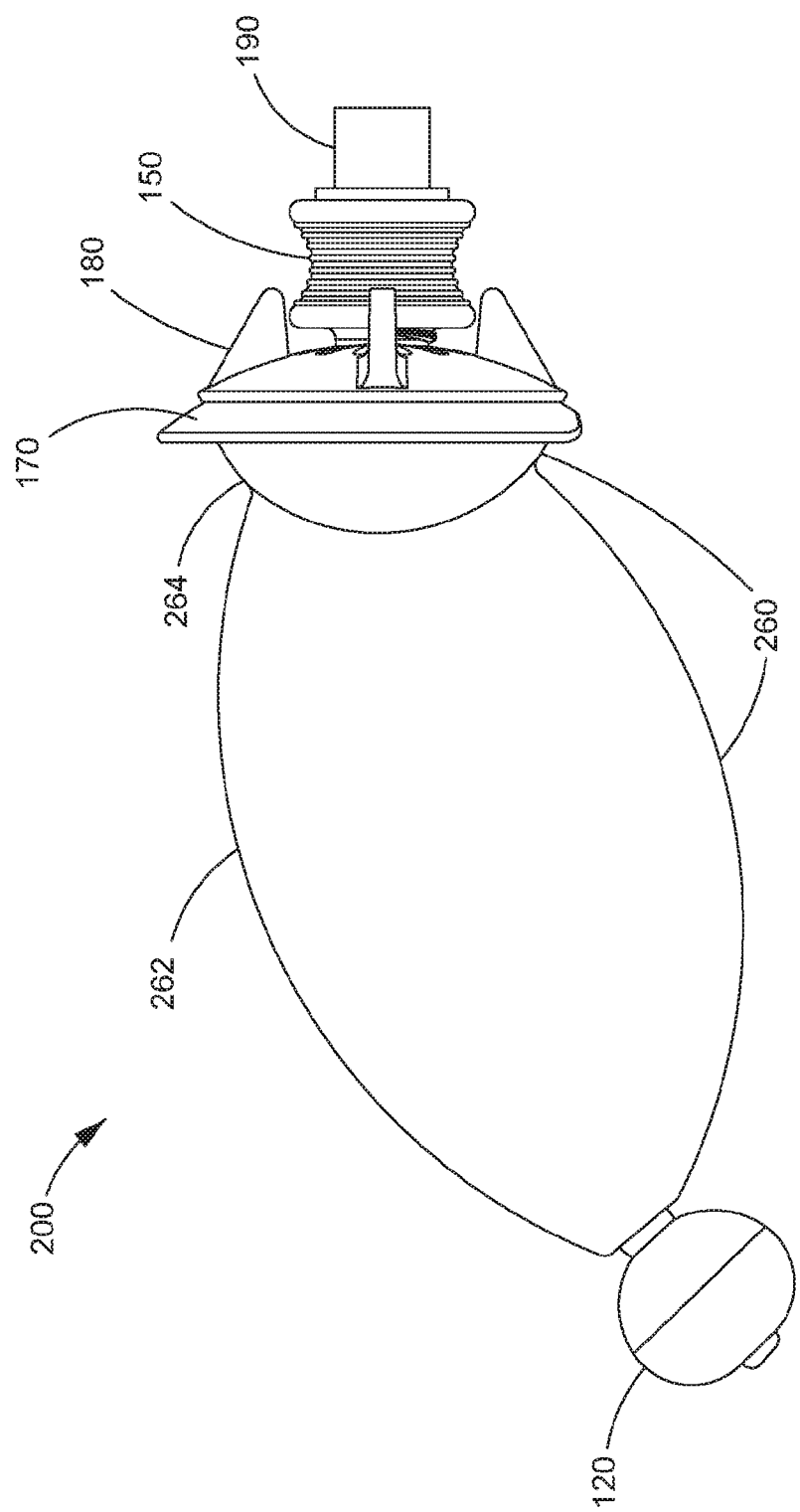
FIGS. 6A-6C illustrate views of a nasal balloon catheter and sponge unit in an inflated state, according to an additional embodiment.
Figure 6B:
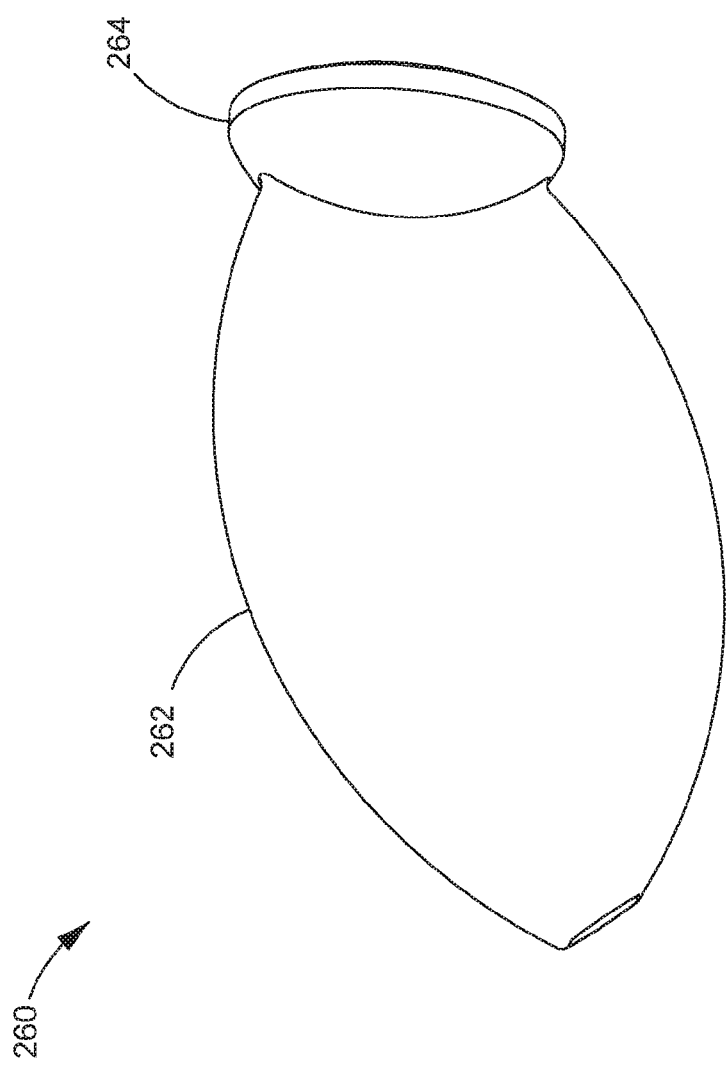
Figure 6C:
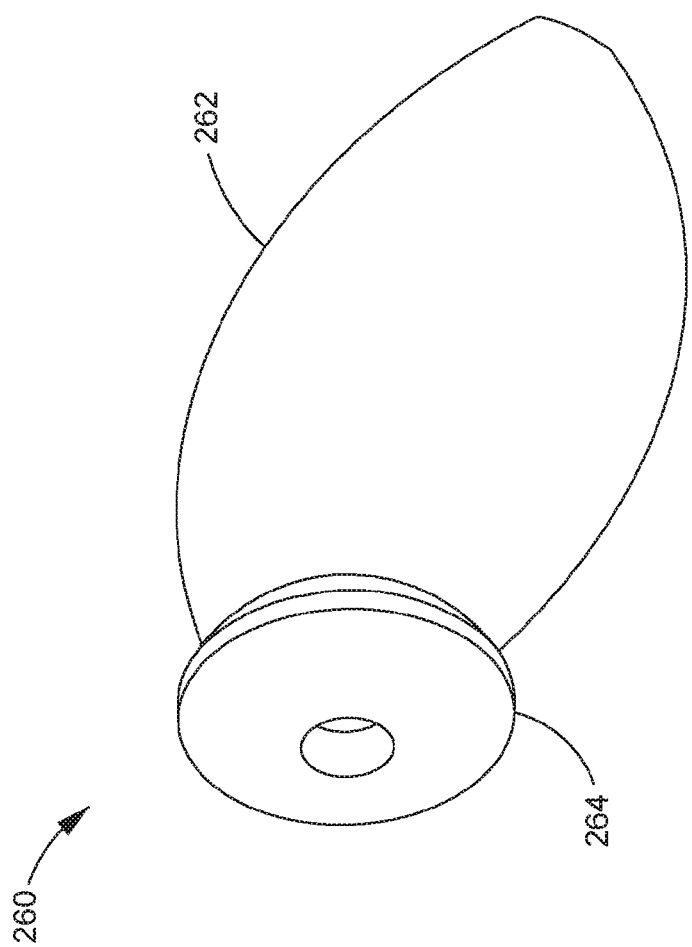

FIGS. 6A-6C provide views of an alternate embodiment of a nasal balloon catheter and sponge unit 200 in which only one balloon (posterior balloon 120) is provided and the anterior balloon is replaced by a full-length expandable sponge 262 that combines with a hemi-dome shaped expandable sponge 264 (forming an expandable sponge 260). The sponge 260 is located on the anterior portion of the catheter core body 110, anterior to the posterior balloon 120. In an embodiment, the expandable sponge 260 surrounds a majority portion (i.e., greater than 50%) of the anterior portion of the catheter core body 110. According to an embodiment, as shown, the sponge 260 is of a three-dimensional elliptical or oval shape (262) and then tapers and expands anteriorly to a hemi-domed shape (264) for fitting and conforming to a nostril of a patient. The sponge 262 also tapers at the posterior end near the posterior balloon 120, in an embodiment as shown in FIGS. 6A-6C. The anterior portion of the sponge 260 has a flat base positioned against the washer 170, allowing for contact with the washer 170 and for compression with posterior movement of the washer 170 and the adjustable nut 180. Various other sizes and shapes of the expandable sponge 260 may be utilized.

In one embodiment, the sponges 262 and 264 are a single unit 260. A central portion is hollow (see FIGS. 6B and 6C), allowing for the expandable sponge 260 to slide over the catheter core body 110, thus providing for a health care provider to increase the pressure via the washer 170 and the adjustable nut 180.

The other components of the nasal balloon catheter and sponge unit 200 are configured and function in an analogous manner as those like numbered components of the nasal balloon catheter and sponge unit 100.

It will be appreciated that the above figures and description provide exemplary, non-limiting configurations. Although the present invention has been described with reference to these exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

I claim:

1. A nasal balloon catheter and sponge unit comprising:
   a catheter core body comprising an anterior portion and a posterior portion;
   a luer lock connected to the catheter core body via a threaded portion attached to an anterior-most portion of the catheter core body;
   an inflation port connected to an anterior end of the luer lock;
   a posterior balloon surrounding at least a portion of the posterior portion of the catheter core body;
   an anterior balloon surrounding at least a portion of the anterior portion of the catheter core body;

an expandable sponge positioned around the anterior-most portion of the catheter core body;
a washer positioned and moveable adjacent and anterior to the sponge on the threaded portion, wherein the washer is sized larger than a nostril of a patient, and is of a substantially round shape with a curved portion at a bottom portion configured to come into contact with the patient; and
an adjustable nut positioned and moveable adjacent and anterior to the washer on the threaded portion;
wherein the catheter core body is insertable into a nasal passage of the patient;
wherein a passageway extends from the inflation port, through the leer lock, through the threaded portion, and through the catheter core body, allowing for a fluid to be introduced through the inflation port and travel through the passageway, exiting at an exit hole located in the posterior portion of the catheter core body to inflate first the posterior balloon and then flow from the posterior balloon into the anterior balloon to inflate the anterior balloon, and
wherein movement of the adjustable nut in a posterior direction along the threaded portion causes corresponding movement of the washer and compression of the expandable sponge in the posterior direction.

2. The nasal balloon catheter and sponge unit of claim 1, wherein the posterior balloon is of a thinner thickness than the anterior balloon, providing for the posterior balloon to inflate prior to the anterior balloon, with both balloons being inflated by way of fluid which has exited the passageway through the exit hole.

3. The nasal balloon catheter and sponge unit of claim 1, wherein the expandable sponge comprises a central hole and a hemi-domed shape with its base facing anteriorly; wherein the expandable sponge is configured to conform to an inside portion of a nostril of the patient when the catheter core body is inserted into the nasal passage of the patient.

4. The nasal balloon catheter and sponge unit of claim 3, wherein the base of the expandable sponge which faces anteriorly is a flat surface which contacts the washer.

5. The nasal balloon catheter and sponge unit of claim 1, wherein the washer comprises a central hole and a soft material.

6. The nasal balloon catheter and sponge unit of claim 5, wherein the central hole of the washer removably receives the catheter core body such that the catheter core body is configured to move back and forth with respect to the washer.

7. The nasal balloon catheter and sponge unit of claim 1, wherein the adjustable nut is configured to be pushed over the threaded portion to compress the sponge in the posterior direction and apply pressure thereto.

8. The nasal balloon catheter and sponge unit of claim 7, wherein the adjustable nut is further configured to decrease pressure on the sponge.

9. The nasal balloon catheter and sponge unit of claim 1, wherein the adjustable nut is one of a rotating nut or a speed nut.

10. The nasal balloon catheter and sponge unit of claim 1, wherein the exit hole fluidly connects the passageway to the posterior balloon and the anterior balloon.

11. The nasal balloon catheter and sponge unit of claim 10, wherein an interior space of the posterior balloon is directly connected to an interior space of the anterior balloon to form a continuous structure which is configured to receive fluid which has exited the exit hole.

12. The nasal balloon catheter and sponge unit of claim 1, wherein the washer is configured to wedge against a nostril of the patient as a result of the posterior movement of the washer that compresses the expandable sponge.

13. The nasal balloon catheter and sponge unit of claim 12, wherein the posterior balloon is configured to seal a nasal choana of the patient due at least in part to the posterior movement of the washer.

14. A nasal balloon catheter and sponge unit, comprising:
a catheter core body comprising an anterior portion and a posterior portion:
a luer lock connected to the catheter core body via a threaded portion attached to an anterior-most portion of the catheter core body;
an inflation port connected at an anterior end of the luer lock;
a posterior balloon surrounding at least a portion of the posterior portion of the catheter core body;
an expandable sponge surrounding at least a portion of the anterior portion of the catheter core body, the expandable sponge including a central hole;
a washer positioned and moveable adjacent and anterior to the expandable sponge on the threaded portion, wherein the washer is sized larger than a nostril of a patient, and is of a substantially round shape with a curved portion at a bottom portion configured to come into contact with the patient; and
an adjustable nut positioned and moveable adjacent and anterior to the washer on the threaded portion;
wherein the catheter core body is insertable into a nasal passage of the patient;
wherein a passageway extends from the inflation port, through the luer lock, through the threaded portion, and through the catheter core body, allowing for a fluid to be introduced through the inflation port and travel through the passageway, exiting at an exit hole located in the posterior portion of the catheter core body to inflate the posterior balloon;
wherein the central hole of the expandable sponge removably receives the catheter core body such that the catheter core body is configured to move back and forth with respect to the expandable sponge, and
wherein movement of the adjustable nut in a posterior direction along the threaded portion causes corresponding movement of the washer and compression of the expandable sponge in the posterior direction.

15. The nasal balloon catheter and sponge unit of claim 14, wherein the expandable sponge is oval shaped, tapering at its ends and expanding anteriorly into a hemi-dome shape at the anterior-most portion of the catheter core body to conform to the inside of a nostril of the patient when the catheter core body is inserted into the nasal passage of the patient.

16. The nasal balloon catheter and sponge unit of claim 15, wherein the oval shaped portion and the hemi-domed shaped portion of the expandable sponge comprise a single unit.

17. The nasal balloon catheter and sponge unit of claim 8, wherein the expandable sponge surrounds a majority portion of the anterior portion of the catheter core body.

18. The nasal balloon catheter and sponge unit of claim 14, wherein the washer comprises a central hole and a soft material.

19. The nasal balloon catheter and sponge unit of claim 14, wherein the adjustable nut is configured to be pushed over the threaded portion to compress the sponge in the posterior direction and apply pressure thereto.

20. The nasal balloon catheter and sponge unit of claim 19, wherein the adjustable nut is further configured to decrease pressure on the sponge.

21. The nasal balloon catheter and sponge unit of claim 14, wherein the adjustable nut is one of a rotating nut or a speed nut.

* * * * *